US010568908B2

(12) United States Patent
O'Reilly et al.

(10) Patent No.: US 10,568,908 B2
(45) Date of Patent: Feb. 25, 2020

(54) METHODS OF TREATING EPSTEIN-BARR VIRUS-ASSOCIATED LYMPHOPROLIFERATIVE DISORDERS BY T CELL THERAPY

(71) Applicant: Memorial Sloan Kettering Cancer Center, New York, NY (US)

(72) Inventors: Richard John O'Reilly, Roxbury, CT (US); Susan Elizabeth Prockop, New York, NY (US); Aisha Nasreen Hasan, Blue Bell, PA (US); Ekaterina Doubrovina, Bronx, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/572,557

(22) PCT Filed: May 11, 2016

(86) PCT No.: PCT/US2016/031784
§ 371 (c)(1),
(2) Date: Nov. 8, 2017

(87) PCT Pub. No.: WO2016/183153
PCT Pub. Date: Nov. 17, 2016

(65) Prior Publication Data
US 2018/0125891 A1 May 10, 2018

Related U.S. Application Data

(60) Provisional application No. 62/160,549, filed on May 12, 2015.

(51) Int. Cl.
A61K 35/17 (2015.01)
A61K 35/15 (2015.01)
A61P 35/00 (2006.01)

(52) U.S. Cl.
CPC .............. *A61K 35/17* (2013.01); *A61K 35/15* (2013.01); *A61P 35/00* (2018.01)

(58) Field of Classification Search
None
See application file for complete search history.

(56) References Cited

U.S. PATENT DOCUMENTS

| 6,723,695 | B1 | 4/2004 | Burrows et al. | |
| 2004/0265325 | A1* | 12/2004 | Diamond | A61K 39/245 424/186.1 |
| 2009/0305324 | A1* | 12/2009 | Kuzushima | C07K 7/06 435/29 |
| 2014/0086888 | A1 | 3/2014 | Heslop et al. | |
| 2015/0273051 | A1* | 10/2015 | Khanna | C07K 14/005 424/230.1 |
| 2016/0375060 | A1* | 12/2016 | O'Reilly | A61K 9/0019 424/93.71 |
| 2017/0319683 | A1* | 11/2017 | O'Reilly | A61K 35/17 |

FOREIGN PATENT DOCUMENTS

| RU | 2506311 C2 | 2/2014 |
| WO | WO 2010/049935 A1 | 5/2010 |

OTHER PUBLICATIONS

Arasaratnam RJ, Leen AM. Adoptive T cell therapy for the treatment of viral infections. Ann Transl Med. Oct. 2015;3(18):278.*
Khanna R, Smith C. Cellular immune therapy for viral infections in transplant patients. Indian J Med Res. Nov. 2013;138(5):796-807.*
Burns and Crawford, Sep. 2004, "Epstein-Barr virus-specific cytotoxic T-lymphocytes for adoptive immunotherapy of post-transplant lymphoproliferative disease," Blood Reviews, 18(3):193-209.
Eiz-Vesper et al., Jan. 2013, "Adoptive T-cell immunotherapy from third-party donors: characterization of donors and set up of a T-cell donor registry," Frontiers in Immunology, 3:410.
Gahn et al., Jan. 2002, "Immunotherapy to reconstitute immunity to DNA viruses," Seminars in Hematology, 39(1):41-47.
Haque et al., Oct. 2001, "Complete regression of posttransplant lymphoproliferative disease using partially HLA-matched Epstein Barr virus-specific cytotoxic T cells," Transplantation,72(8): 1399-1402.
Haque et al., Aug. 2007, "Allogeneic cytotoxic T-cell therapy for EBV-positive posttransplantation lymphoproliferative disease: results of a phase 2 multicenter clinical trial," Blood, 110(4):1123-1131 (Published online Apr. 27, 2007).
Haque et al., Aug. 2002, "Treatment of Epstein-Barr-virus-positive post-transplantation lymphoproliferative disease with partly HLA-matched allogeneic cytotoxic T cells," Lancet, 360(9331):436-442.
Leen et al, Jun. 2013, "Multicenter study of banked third-party virus-specific T cells to treat severe viral infections after hematopoietic stem cell transplantation," Blood, 121(26):5113-5123 (Published online Apr. 22, 2013).
Leen et al., Oct. 2006, "Monoculture-derived T lymphocytes specific for multiple viruses expand and produce clinically relevant effects in immunocompromised individuals," Nature Medicine, 12(10):1160-1166 (Published online Sep. 24, 2006).
Louis et al., Nov.-Dec. 2010, "Adoptive transfer of EBV-specific T cells results in sustained clinical responses in patients with locoregional nasopharyngeal carcinoma," Journal of Immunotherapy, 33(9):983-990.
Papadopoulou et al., Jun. 2014, "Activity of broad-spectrum T cells as treatment for AdV, EBV, CMV, BKV, and HHV6 infections after HSCT," Science Translational Medicine, 6(242):242ra83.
Sili et al., Jan. 2012, "Production of good manufacturing practice-grade cytotoxic T lymphocytes specific for Epstein-Barr virus, cytomegalovirus and adenovirus to prevent or treat viral infections post-allogeneic hematopoietic stem cell transplant," Cytotherapy, 14(1):7-11.

(Continued)

*Primary Examiner* — Benjamin P Blumel
(74) *Attorney, Agent, or Firm* — Jones Day

(57) ABSTRACT

The invention relates to methods of treating an EBV-LPD (Epstein-Barr Virus-associated lymphoproliferative disorder) in a human patient who has failed combination chemotherapy to treat the EBV-LPD and/or radiation therapy to treat the EBV-LPD, comprising administering to the human patient a population of allogeneic T cells comprising EBV-specific T cells.

37 Claims, No Drawings

(56) References Cited

OTHER PUBLICATIONS

Straathof et al., Mar. 2005, "Treatment of nasopharyngeal carcinoma with Epstein-Barr virus—specific T lymphocytes," Blood, 105(5):1898-1904 (Published online Nov. 12, 2004).
Sukdolak et al., Oct. 2013, "CMV-, EBV- and ADV-specific T cell immunity: screening and monitoring of potential third-party donors to improve post-transplantation outcome," Biology of Blood and Marrow Transplantation, 19(10):1480-1492 (Published online Jul. 23, 2013).
Uhlin et al., Oct. 2012, "Rapid salvage treatment with virus-specific T cells for therapy-resistant disease," Clinical Infectious Diseases, 55(8):1064-1073 (Published online Jul. 17, 2012).
Wilkie et al., Jul.-Aug. 2004, "Establishment and characterization of a bank of cytotoxic T lymphocytes for immunotherapy of epstein-barr virus-associated diseases," Journal of Immunotherapy, 27(4):309-316.
Barker et al., Dec. 2010, "Successful treatment of EBV-associated posttransplantation lymphoma after cord blood transplantation using third-party EBV-specific cytotoxic T lymphocytes," Blood, 116(23):5045-5049 (Published online Sep. 8, 2010).
Doubrovina et al., Mar. 2012, "Adoptive immunotherapy with unselected or EBV-specific T cells for biopsy-proven EBV+ lymphomas after allogeneic hematopoietic cell transplantation," Blood, 119(11):2644-2656 (Published online Dec. 2, 2011).
Hasan et al., Aug. 2009, "A panel of artificial APCs expressing prevalent HLA alleles permits generation of cytotoxic T cells specific for both dominant and subdominant viral epitopes for adoptive therapy," The Journal of Immunology, 183(4):2837-2850 (Published online Jul. 27, 2009).
Koehne et al., Jul. 2000, "Rapid selection of antigen-specific T lymphocytes by retroviral transduction," Blood, 96(1):109-117.
Koehne et al., Mar. 2002, "Quantitation, selection, and functional characterization of Epstein-Barr virus-specific and alloreactive T cells detected by intracellular interferon-gamma production and growth of cytotoxic precursors," Blood, 99(5):1730-1740.
Prockop et al., Feb. 2014, "Third party donor derived EBV specific T cells for the treatment of refractory EBV-related post-transplant lymphomas," Biology of Blood and Marrow Transplantation, 20(2):S49-S50.
O'Reilly, meeting abstract for the oral presentation on Oct. 31, 2014 at the 76th Annual Meeting of the Japanese Society of Hematology, held Oct. 31-Nov. 2, 2014, Osaka, Japan.
O'Reilly et al., Sep. 2011, "Novel strategies for adoptive therapy following HLA disparate transplants," Best Practice & Research Clinical Haematology, 24(3):381-391.
O'Reilly et al., May 2007, "Adoptive transfer of antigen-specific T-cells of donor type for immunotherapy of viral infections following allogeneic hematopoietic cell transplants," Immunologic Research, 38(1-3):237-250.
O'Reilly et al., Jun. 2010, "Adoptive transfer of unselected or leukemia-reactive T-cells in the treatment of relapse following allogeneic hematopoietic cell transplantation," Seminars in Immunology, 22(3):162-172 (Published online May 26, 2010).
"Biological therapy in treating patients at high-risk or with lymphoma, lymphoproliferative disease, or malignancies," ClinicalTrials.gov, accessed at https://clinicaltrials.gov/ct2/show/NCT00002663?term=NCT00002663&rank=1, first accessed on Oct. 21, 2014, 5 pages.
"Therapeutic effects of Epstein-Barr virus immune T-lymphocytes derived from a normal HLA-compatible or partially-matched third-party donor in the treatment of EBV lymphoproliferative disorders and EBV-associated malignancies," ClinicalTrials.gov, accessed at http://www.clinicaltrials.gov/ct2/show/NCT01498484?term=NCT01498484&rank=1, first accessed on Oct. 21, 2014, 5 pages.
Prockop, "Adoptive immunotherapy with banked virus specific 3rd party donor T-cells for CMV infections and EBV LPD complicating hematopoietic cell transplants," slide presentation on Oct. 31, 2014 at the 76th Annual Meeting of the Japanese Society of Hematology, held Oct. 31-Nov. 2, 2014, Osaka, Japan, 43 pages.
Prockop, "Third party donor T cells for the treatment of CMV infection and EBV lymphoma in immunodeficient patients," slide presentation on May 22, 2014 at the 9th Meeting of the EBMT Pediatric Diseases WP, held May 21-23, 2014, Jerusalem, Israel, 47 pages.
Prockop, "Third party donor derived EBV specific T cells for the treatment of refractory lymphoma in immunodeficient recipients," slide presentation on Mar. 1, 2014 at the ASBMT 2014 BMT Tandem Meetings held Feb. 26-Mar. 2, 2014, Grapevine, Texas, United States, 22 pages.
Prockop, "Epstein-Barr virus (EBV)-specific cytotoxic T lymphocytes (EBV-CTLs) for treatment of rituximab-refractory EBV-associated lymphoproliferative disorder (EBV-LPD)," slide presentation on Apr. 19, 2015 at the 2015 AACR Anual Meeting held Apr. 18-22, 2015, Philadelphia, Pennsylvania, United States, 25 pages.
Khanna et al., Aug. 1999, "Activation and adoptive transfer of Epstein-Barr virus-specific cytotoxic T cells in solid organ transplant patients with posttransplant lymphoproliferative disease," Proceedings of the National Academy of Sciences of the United States of America, 96(18):10391-10396.
Comoli et al., Apr. 2002, "Infusion of autologous Epstein-Barr virus (EBV)-specific cytotoxic T cells for prevention of EBV-related lymphoproliferative disorder in solid organ transplant recipients with evidence of active virus replication," Blood, 99(7):2592-2598.
Gottschalk et al., Jan. 2015, "Adoptive T-cell immunotherapy," Current Topics in Microbiology and Immunology, 391:427-454.
Gandhi et al., May 2007, "Immunity, homing and efficacy of allogeneic adoptive immunotherapy for posttransplant lymphoproliferative disorders," American Journal of Transplantation, 7(5):1293-1299 (Published online Apr. 8, 2007).
Tse and Kwong, Jan. 2015, "Epstein Barr virus-associated lymphoproliferative diseases: the virus as a therapeutic target," Experimental & Molecular Medicine, 47:e136.
Lucas et al., Mar. 1996, "The development of cellular immunity to Epstein-Barr virus after allogeneic bone marrow transplantation," Blood, 87(6):2594-2603.
Rooney et al., Sep. 1998, "Infusion of cytotoxic T cells for the prevention and treatment of Epstein-Barr virus-induced lymphoma in allogeneic transplant recipients," Blood, 92(5):1549-1555.
Prockop et al., "Epstein-Barr virus-specific cytotoxic T lymphocytes for treatment of rituximab-refractory Epstein-Barr virus-associated lymphoproliferative disorder," meeting abstract for the 2015 AACR Anual Meeting held Apr. 18-22, 2015, Philadelphia, Pennsylvania, United States, published Mar. 18, 2015, 2 pages.
American Association for Cancer Research (AACR) Press Release entitled "New T cell-based immunotherapy shows promise for lethal stem cell transplant complication," dated Apr. 19, 2015, 3 pages.
Amarnath and Fowler, Jan. 2012, "Harnessing autophagy for adoptive T cell therapy," Immunotherapy, 4(1):1-4.
Heslop et al., Feb. 2010, "Long-term outcome of EBV-specific T-cell infusions to prevent or treat EBV-related lymphoproliferative disease in transplant recipients," Blood, 115(5):925-935 (Published online Oct. 30, 2009).
International Search Report, Information on Search Strategy, and Written Opinion of the International Searching Authority, for International Patent Application No. PCT/US2016/031784, dated Jul. 18, 2016, 12 pages.
Elstrom et al., 2006, "Treatment of PTLD with rituximab or chemotherapy," Am J Transplant 6(3):569-576.
Webber et al, 2004, "Anti-CD20 monoclonal antibody (rituximab) for refractory PTLD after pediatric solid organ transplantation: multicenter experience from a registry and from a prospective clinical trial," Blood 104: Abstract 746.
Messahel et al, 2006, "Single agent efficacy of rituximab in childhood immunosuppression related lymphoproliferative disease: a United Kingdom Children's Cancer Study Group (UKCCSG) retrospective review," Leuk Lymphoma 47(12):2584-2589.
Gross et al., Nov. 2012, "Low-dose chemotherapy and rituximab for posttransplant lymphoproliferative disease (PTLD): a Children's Oncology Group Report," Am J Transplant 12(11):3069-3075 (Published online Aug. 6, 2012).

(56) References Cited

OTHER PUBLICATIONS

Rooney et al., Jan. 1995, "Use of gene-modified virus-specific T lymphocytes to control Epstein-Barr-virus-related lymphoproliferation," Lancet, 345(8941):9-13.
Gottschalk et al., Feb. 2001, "An Epstein-Barr virus deletion mutant associated with fatal lymphoproliferative disease unresponsive to therapy with virus-specific CTLs," Blood 97(4):835-843.
Grandien, May 1996, "Viral diagnosis by antigen detection techniques," Clin Diagn Virol 5(2-3):81-90.
Gulley and Tang, Jul. 2008, "Laboratory assays for Epstein-Barr virus-related disease," J Mol Diagn 10(4):279-292.
Witzig et al., Jun. 2007, "Treatment of Benign Orbital Pseudolymphomas With the Monoclonal Anti-CD20 Antibody Rituximab," Mayo Clin Proc 82(6):692-699.
Lucas et al., May 2004, "Adoptive immunotherapy with allogeneic Epstein-Barr virus (EBV)-specific cytotoxic T-lymphocytes for recurrent, EBV-positive Hodgkin disease," Cancer 100(9):1892-1901.
Sun et al., Sep. 2002, "Safety of allogeneic Epstein-Barr virus (EBV)-specific cytotoxic T lymphocytes for patients with refractory EBV-related lymphoma," Br J Haematol 118(3):799-808.
V. Gurtsevich, 2010, "The role of Epstein-Barr virus in human hematopoietic neoplasms," Oncohaematology, 3(3): 222-234 (incl. English abstract).
Hasan et al., Feb. 2014, "Generation and characterization of a third party GMP grade bank of CMV specific T-cells for adoptive immunotherapy of CMV infections in recipients of HSCT from cord blood or seronegative donors," Biology of Blood and Marrow Transplantation, 20(2):S131-S132.

\* cited by examiner

METHODS OF TREATING EPSTEIN-BARR VIRUS-ASSOCIATED LYMPHOPROLIFERATIVE DISORDERS BY T CELL THERAPY

CROSS-REFERENCE TO RELATED APPLICATIONS

This application is a national stage of International Patent Application No. PCT/US2016/031784, filed May 11, 2016, which claims the benefit of U.S. provisional application No. 62/160,549, filed on May 12, 2015, each of which is incorporated by reference herein in its entirety.

GOVERNMENT RIGHTS STATEMENT

This invention was made with government support under CA055349 awarded by National Institutes of Health. The government has certain rights in the invention.

1. FIELD

Disclosed herein are methods of treating an EBV-LPD (Epstein-Barr Virus-associated lymphoproliferative disorder) in a human patient who has failed combination chemotherapy to treat the EBV-LPD and/or radiation therapy to treat the EBV-LPD, comprising administering to the human patient a population of allogeneic T cells comprising EBV-specific T cells.

2. BACKGROUND

Epstein-Barr Virus-associated lymphoproliferative disorders (EBV-LPDs) are a significant cause of morbidity and mortality for solid organ transplant recipients, hematopoietic stem cell transplant recipients, and other immunocompromised patients. Different therapies have been developed to treat EBV-LPDs, such as chemotherapy, combination chemotherapy, radiation therapy, therapy with rituximab (an anti-CD20 monoclonal antibody), and cellular immunotherapy (see, for example, Elstrom et al., 2006, Am J Transplant 6:569-576; Haque et al, 2001, Transplantation 72:1399-1402; Haque et al, 2002, Lancet 360:435-442; Gandhi et al, 2007, American Journal of Transplantation 7:1293-1299; and Doubrovina, E., et al., Blood, 2012. 119: 2644-2656). In situations where a first-line therapy has failed, later lines of therapy are often attempted. For example, for many SOT recipients, especially those with low grade disease, the first-line of treatment is decreasing dosage of immunosuppressant given to the patient. Several authors have reported efficacy of single agent rituximab in patients who failed to respond to reduction in immunosuppressant dosage (see, for example, Webber et al, 2004, Blood 104: Abstract 746; and Messahel et al, 2006, Leuk Lymphoma 47:2584-2589). If patients relapse after responding to rituximab or fail to respond to rituximab, there is no consensus in terms of whether re-treating with single agent rituximab is worthwhile and many centers will proceed to combination chemotherapy. The Children's Oncology Group recently completed a trial of low dose cyclophosphamide, steroids and rituximab with 2 year EFS (event free survival) of 71% and OS (overall survival) of 83% (Gross et al., 2012, Am J Transplant 12:3069-3075). In adult patients the treatment is more varied and includes R-CHOP (a therapy regimen with cyclophosphamide, doxorubicin, vincristine, prednisone, and rituximab) or DA-EPOCH (Dose-Adjusted EPOCH, which is a therapy regimen with etoposide, prednisone, vincristine, cyclophosphamide, and doxorubicin). In patients with CNS (central nervous system) involvement of EBV-LPD, regimens include intrathecal rituximab, radiation or high dose methotrexate alone for CNS only disease, or in combination for systemic and CNS disease.

EBV-LPDs resistant to a previous therapy that has shown to be effective clinically (for example, combination chemotherapy, radiation therapy, or therapy with rituximab) are harder to treat. The greater the degree of efficacy the previous therapy has shown to demonstrate clinically, and the more therapies the patient has failed, the greater the expectation of difficulty in achieving successful treatment by a later-line therapy. An EBV-LPD that is resistant to a previous therapy is usually more aggressive. This is especially true when the previous therapy is chemotherapy or radiation therapy, which often leads to or selects for mutated tumor cells, resulting in a much more aggressive disease. First-line therapies are usually selected based on their desirable combination of safety and efficacy, while later lines of therapy are usually considered less desirable in terms of their safety and/or efficacy profiles. Thus, there is a need for methods of treating EBV-LPD in patients who have failed combination chemotherapy and/or radiation therapy that have desirable safety and efficacy profiles.

Citation of a reference herein shall not be construed as an admission that such is prior art to the present disclosure.

3. SUMMARY OF THE INVENTION

The present invention relates to methods of treating an EBV-LPD (Epstein-Barr Virus-associated lymphoproliferative disorder) in a human patient who has failed combination chemotherapy to treat the EBV-LPD and/or radiation therapy to treat the EBV-LPD.

In one aspect, provided herein are methods of treating an EBV-LPD in a human patient comprising administering to the human patient a population of allogeneic T cells comprising EBV-specific T cells; wherein the human patient has failed a combination chemotherapy to treat the EBV-LPD, and wherein the population of allogeneic T cells is restricted by an human leukocyte antigen (HLA) allele shared with cells of the EBV-LPD. (The population of allogeneic T cells is human.) In certain embodiments, the EBV-LPD is resistant to the combination chemotherapy to treat the EBV-LPD. In certain embodiments, the human patient has been taken off the combination chemotherapy due to intolerance of the combination chemotherapy. In a specific embodiment, the combination chemotherapy that the human patient has failed comprises therapy with cyclophosphamide and prednisone. In a further specific embodiment, the combination chemotherapy that the human patient has failed comprises a low-dose cyclophosphamide and prednisone regimen. In another specific embodiment, the combination chemotherapy that the human patient has failed comprises therapy with cyclophosphamide and methylprednisolone. In another further specific embodiment, the combination chemotherapy that the human patient has failed comprises a low-dose cyclophosphamide and methylprednisolone regimen.

In specific embodiments, the human patient also has failed multiple different combination chemotherapies to treat the EBV-LPD. In a particular embodiment, the EBV-LPD is resistant to the multiple different combination chemotherapies to treat the EBV-LPD. In another particular embodiment, the human patient has been taken off the multiple different combination chemotherapies due to intolerance of the multiple different combination chemotherapies. In a specific embodiment, at least one of the multiple different combination chemotherapies that the human patient has failed comprises therapy with cyclophosphamide and prednisone. In a further specific embodiment, at least one of the multiple different combination chemotherapies that the human patient has failed comprises a low-dose cyclophosphamide and prednisone regimen. In another specific embodiment, at least one of the multiple different combination chemotherapies that the human patient has failed comprises therapy with cyclophosphamide and methylprednisolone. In another further specific embodiment, at least one of the multiple different combination chemotherapies that the human patient has failed comprises a low-dose cyclophosphamide and methylprednisolone regimen.

In specific embodiments, the human patient who has failed a combination chemotherapy to treat the EBV-LPD (or multiple different combination chemotherapies) also has failed a radiation therapy to treat the EBV-LPD. In a particular embodiment, the EBV-LPD is resistant to the radiation therapy to treat the EBV-LPD. In another particular embodiment, the human patient has been taken off the radiation therapy due to intolerance of the radiation therapy.

In another aspect, provided herein are methods of treating an EBV-LPD in a human patient comprising administering to the human patient a population of allogeneic T cells comprising EBV-specific T cells; wherein the human patient has failed a radiation therapy to treat the EBV-LPD, and wherein the population of allogeneic T cells is restricted by an HLA allele shared with cells of the EBV-LPD. In certain embodiments, the EBV-LPD is resistant to the radiation therapy to treat the EBV-LPD. In certain embodiments, the human patient has been taken off the radiation therapy due to intolerance of the radiation therapy.

In various embodiments, wherein the EBV-LPD is a disorder of cells of B cell lineage, in addition to failing a combination chemotherapy (or multiple different combination chemotherapies) and/or a radiation therapy as described above, the human patient also has failed a therapy with an anti-CD20 monoclonal antibody to treat the EBV-LPD. In certain embodiments, the EBV-LPD is resistant to the therapy with the anti-CD20 monoclonal antibody to treat the EBV-LPD. In certain embodiments, the human patient has been taken off the therapy with the anti-CD20 monoclonal antibody due to intolerance of the therapy with the anti-CD20 monoclonal antibody. In a specific embodiment, the anti-CD20 monoclonal antibody is rituximab.

In specific embodiments, in addition to being restricted by an HLA allele shared with the EBV-LPD, the population of allogeneic T cells comprising EBV-specific T cells shares at least 2 out of 8 HLA alleles with cells of the EBV-LPD. In a specific embodiment, the 8 HLA alleles are two HLA-A alleles, two HLA-B alleles, two HLA-C alleles, and two HLA-DR alleles.

In specific embodiments, the methods of treating an EBV-LPD as described herein further comprise prior to the administering step a step of ascertaining at least one HLA allele of cells of the EBV-LPD by high-resolution typing.

In various embodiments, the methods of treating an EBV-LPD further comprise prior to the administering step a step of generating the population of allogeneic T cells in vitro.

In specific embodiments, the step of generating the population of allogeneic T cells in vitro comprises sensitizing allogeneic T cells to one or more EBV antigens.

In certain embodiments, the step of generating the population of allogeneic T cells in vitro comprises sensitizing allogeneic T cells using EBV-transformed B cells. In a specific embodiment, the step of generating the population of allogeneic T cells in vitro comprises sensitizing allogeneic T cells using EBV strain B95.8-transformed B cells.

In certain embodiments, the step of generating the population of allogeneic T cells in vitro comprises sensitizing allogeneic T cells using dendritic cells, cytokine-activated monocytes, or peripheral blood mononuclear cells. In specific embodiments, the step of sensitizing allogeneic T cells using dendritic cells, cytokine-activated monocytes, or peripheral blood mononuclear cells comprises loading the dendritic cells, the cytokine-activated monocytes, or the peripheral blood mononuclear cells with at least one immunogenic peptide derived from one or more EBV antigens. In specific embodiments, the step of sensitizing allogeneic T cells using dendritic cells, cytokine-activated monocytes, or peripheral blood mononuclear cells comprises loading the dendritic cells, the cytokine-activated monocytes, or the peripheral blood mononuclear cells with a pool of overlapping peptides derived from one or more EBV antigens.

In certain embodiments, the step of generating the population of allogeneic T cells in vitro comprises sensitizing allogeneic T cells using artificial antigen-presenting cells (AAPCs). In specific embodiments, the step of sensitizing allogeneic T cells using AAPCs comprises loading the AAPCs with at least one immunogenic peptide derived from one or more EBV antigens. In specific embodiments, the step of sensitizing allogeneic T cells using AAPCs comprises loading the AAPCs with a pool of overlapping peptides derived from one or more EBV antigens. In specific embodiments, the step of sensitizing allogeneic T cells using AAPCs comprises engineering the AAPCs to express at least one immunogenic EBV peptide or protein in the AAPCs.

In specific embodiments, the step of generating the population of allogeneic T cells in vitro further comprises, after sensitizing, cryopreserving the allogeneic T cells.

In specific embodiments, the methods of treating an EBV-LPD as described herein further comprise, before the administering step, steps of thawing cryopreserved EBV-antigen sensitized allogeneic T cells, and expanding the allogeneic T cells in vitro, to produce the population of allogeneic T cells.

In certain embodiments, the methods of treating an EBV-LPD as described herein further comprise, before the administering step, a step of thawing a cryopreserved form of the population of allogeneic T cells.

In various embodiments, the population of allogeneic T cells is derived from a T cell line. In certain embodiments, the methods of treating an EBV-LPD as described herein further comprise, before the administering step, a step of selecting the T cell line from a bank of a plurality of cryopreserved T cell lines. In certain embodiments, the methods of treating an EBV-LPD as described herein further comprise, before the administering step, a step of thawing a cryopreserved form of the T cell line. In specific embodiments, the methods of treating an EBV-LPD as described herein further comprises, before the administering step, a step of expanding the T cell line in vitro.

In specific embodiments, the EBV-specific T cells administered in accordance with the methods described herein recognizes an EBV antigen that is EBNA1, EBNA2, EBNA3A, EBNA3B, EBNA3C, LMP1 or LMP2.

In certain embodiments, the administering is by infusion of the population of allogeneic T cells. In some embodiments, the infusion is bolus intravenous infusion. In certain embodiments, the administering comprises administering at least about $1 \times 10^5$ T cells of the population of allogeneic T cells per kg per dose per week to the human patient. In some embodiments, the administering comprises administering about $1 \times 10^6$ to about $2 \times 10^6$ T cells of the population of allogeneic T cells per kg per dose per week to the human patient. In a specific embodiment, the administering comprises administering about $1 \times 10^6$ T cells of the population of allogeneic T cells per kg per dose per week to the human patient. In another specific embodiment, the administering comprises administering about $2 \times 10^6$ T cells of the population of allogeneic T cells per kg per dose per week to the human patient.

In certain embodiments, the methods of treating an EBV-LPD as described herein comprise administering at least 2 doses of the population of allogeneic T cells to the human patient. In specific embodiments, the methods of treating an EBV-LPD as described herein comprise administering 2, 3, 4, 5, or 6 doses of the population of allogeneic T cells to the human patient.

In certain embodiments, the methods of treating an EBV-LPD as described herein comprise administering a first cycle of one dose per week of the population of allogeneic T cells for 3 consecutive weeks followed by a washout period during which no dose of the population of allogeneic T cells is administered, followed by a second cycle of the one dose per week of the population of allogeneic T cells for 3 consecutive weeks. In specific embodiments, the methods of treating an EBV-LPD as described herein comprise administering two, three, four, five, or six cycles of one dose per week of the population of allogeneic T cells for 3 consecutive weeks, each cycle separated by a washout period during which no dose of the population of allogeneic T cells is administered. In a specific embodiment, the washout period is about three weeks.

In certain embodiments, the methods of treating an EBV-LPD further comprise, after administering to the human patient the population of allogeneic T cells, administering to the human patient a second population of allogeneic T cells comprising EBV-specific T cells; wherein the second population of allogeneic T cells is restricted by a different HLA allele shared with cells of the EBV-LPD. In a specific embodiment, the methods of treating an EBV-LPD comprise administering a first cycle of one dose per week of the population of allogeneic T cells for 3 consecutive weeks followed by a washout period during which no dose of the population of allogeneic T cells is administered, followed by a second cycle of one dose per week of the second population of allogeneic T cells for 3 consecutive weeks. In a further specific embodiment, the washout period is about three weeks.

In certain embodiments, the human patient has no response, an incomplete response, or a suboptimal response after administering the population of allogeneic T cells and prior to administering the second population of allogeneic T cells.

The human patient can be anyone who has an EBV-LPD and who has failed combination chemotherapy to treat the EBV-LPD (and in some embodiments, also has failed therapy with an anti-CD20 monoclonal antibody) and/or radiation therapy (and in some embodiments, also has failed therapy with an anti-CD20 monoclonal antibody).

In a specific embodiment, the EBV-LPD is an EBV-positive lymphoma. In specific embodiments, the EBV-LPD treated in accordance with a method described herein is present in the central nervous system of the human patient. In a specific embodiment, the EBV-LPD treated in accordance with a method described herein is present in the brain of the human patient.

In some embodiments, the human patient has been the recipient of a solid organ transplant from a transplant donor. In some embodiments, the human patient has been the recipient of multiple organ transplants (for example, heart and lung transplants, or kidney and pancreas transplants). The solid organ transplant can be, but is not limited to, a kidney transplant, a liver transplant, a heart transplant, an intestinal transplant, a pancreas transplant, a lung transplant, or a combination thereof. In a specific embodiment, the solid organ transplant is a kidney transplant. In another specific embodiment, the solid organ transplant is a liver transplant. In some embodiments, the human patient has been the recipient of a hematopoietic stem cell transplant (HSCT) from a transplant donor. The HSCT can be a bone marrow transplant, a peripheral blood stem cell transplant, or a cord blood transplant. In specific embodiments, the population of allogeneic T cells is derived from a donor other than the transplant donor.

4. DETAILED DESCRIPTION

The present invention relates to methods of treating an EBV-LPD (Epstein-Barr Virus-associated lymphoproliferative disorder) in a human patient who has failed combination chemotherapy to treat the EBV-LPD and/or radiation therapy to treat the EBV-LPD. This invention provides a T cell therapy method that is effective in treating EBV-LPD that is resistant to combination chemotherapy or to radiation therapy, and thus finds use as a later-line therapy with low toxicity.

In one aspect, provided herein are methods of treating an EBV-LPD in a human patient comprising administering to the human patient a population of allogeneic T cells comprising EBV-specific T cells; wherein the human patient has failed a combination chemotherapy to treat the EBV-LPD, and wherein the population of allogeneic T cells is restricted by an human leukocyte antigen (HLA) allele shared with cells of the EBV-LPD. In certain embodiments, the EBV-LPD is resistant to the combination chemotherapy to treat the EBV-LPD. In certain embodiments, the human patient has been taken off the combination chemotherapy due to intolerance of the combination chemotherapy. In specific embodiments, the human patient also has failed multiple different combination chemotherapies to treat the EBV-LPD. In a particular embodiment, the EBV-LPD is resistant to the multiple different combination chemotherapies to treat the EBV-LPD. In another particular embodiment, the human patient has been taken off the multiple different combination chemotherapies due to intolerance of the multiple different combination chemotherapies. In specific embodiments, the human patient also has failed a radiation therapy to treat the EBV-LPD. In a particular embodiment, the EBV-LPD is resistant to the radiation therapy to treat the EBV-LPD. In another particular embodiment, the human patient has been taken off the radiation therapy due to intolerance of the radiation therapy.

In another aspect, provided herein are methods of treating an EBV-LPD in a human patient comprising administering to the human patient a population of allogeneic T cells comprising EBV-specific T cells; wherein the human patient has failed a radiation therapy to treat the EBV-LPD, and wherein the population of allogeneic T cells is restricted by an HLA allele shared with cells of the EBV-LPD. In certain embodiments, the EBV-LPD is resistant to the radiation therapy to treat the EBV-LPD. In certain embodiments, the human patient has been taken off the radiation therapy due to intolerance of the radiation therapy.

In various embodiments, wherein the EBV-LPD is a disorder of cells of B cell lineage, in addition to failing a combination chemotherapy (or multiple different combination chemotherapies) and/or a radiation therapy as described above, the human patient also has failed a therapy with an anti-CD20 monoclonal antibody (for example, rituximab) to treat the EBV-LPD. In certain embodiments, the EBV-LPD is resistant to the therapy with the anti-CD20 monoclonal antibody to treat the EBV-LPD. In certain embodiments, the human patient has been taken off the therapy with the anti-CD20 monoclonal antibody due to intolerance of the therapy with the anti-CD20 monoclonal antibody.

A human patient is considered to have failed a therapy (e.g., combination chemotherapy, radiation therapy, and/or therapy with anti-CD20 monoclonal antibody) of EBV-LPD if the EBV-LPD is resistant to the therapy and/or if the human patient has been taken off the therapy due to intolerance of the therapy (for example, due to toxicity of the therapy in view of the patient's age or condition). An EBV-LPD is considered resistant to a therapy (e.g., combination chemotherapy, radiation therapy, or therapy with anti-CD20 monoclonal antibody), if the EBV-LPD has no response, or has an incomplete response (a response that is less than a complete remission), or progresses, or relapses after the therapy. A complete remission is a complete resolution of all clinical and radiologic evidence of the disease, optionally confirmed by biopsy of affected tissues, lasting for at least three weeks following completion of the therapy.

4.1. Combination Chemotherapies, Radiation Therapies, and Anti-CD20 Antibodies

Combination chemotherapy involves the therapeutic use over the same treatment period of two or more different chemotherapeutic agents to treat cancer. A chemotherapeutic agent is an anti-cancer cytotoxic chemical drug, generally a small molecule, synthetic organic compound, and is distinct from other types of anti-cancer agents such as biopolymers and cells. Thus, chemotherapeutic agents are not nucleic acids, proteins (for example, antibodies), or immune cells (for example, T cells). Combination chemotherapy is often attempted in order to minimize potential resistance of the cancer (e.g., EBV-LPD) to the therapy. This is because cancer cells could mutate to become resistant to a single chemotherapeutic agent, but by using different chemotherapeutic agents it would be more difficult for the cancer to mutate so as to develop resistance to the combination. Therefore, a combination chemotherapy-resistant EBV-LPD is usually considered harder to treat than a single agent-resistant EBV-LPD.

The present invention provides for treatment of a human patient with EBV-LPD who has failed a combination chemotherapy to treat the EBV-LPD. The combination chemotherapy that the human patient has failed can be any known in the art for treatment of a LPD (lymphoproliferative disorder). Exemplary combination chemotherapies include, but are not limited to (the combinations being of the chemotherapeutic agents in parentheses): 7+3 (7 days of cytarabine plus 3 days of an anthracycline antibiotic, either daunorubicin or idarubicin), ABVD (doxorubicin, bleomycin, vinblastine, dacarbazine), BACOD (bleomycin, doxorubicin, cyclophosphamide, vincristine, dexamethasone), BEACOPP (bleomycin, etoposide, doxorubicin, cyclophosphamide, vincristine, procarbazine, prednisone), Dose-Escalated BEACOPP, CBV (cyclophosphamide, carmustine, etoposide), COP (cyclophosphamide, vincristine, and prednisone or prednisolone), CHOEP (cyclophosphamide, doxorubicin, etoposide, vincristine, prednisone), CEOP (cyclophosphamide, etoposide, vincristine, prednisone), CEPP (cyclophosphamide, etoposide, procarbazine, prednisone), ChlVPP (chlorambucil, vincristine, procarbazine, prednisone, etoposide, vinblastine, doxorubicin), CHOP (cyclophosphamide, doxorubicin, vincristine, prednisone), DCEP (dexamethasone, cyclophosphamide, etoposide, platinum agent), DHAP (dexamethasone, cytarabine, platinum agent), DICE (dexamethasone, ifosfamide, cisplatin, etoposide), DT-PACE (dexamethasone, thalidomide, platinum agent, doxorubicin, cyclophosphamide, etoposide), EPOCH (etoposide, prednisone, vincristine, cyclophosphamide, doxorubicin), DA-EPOCH (Dose-Adjusted EPOCH), ESHAP (etoposide, methylprednisolone, cytarabine, cisplatin), FCM (fludarabine, cyclophosphamide, mitoxantrone), FM (fludarabine, mitoxantrone), FLAG (fludarabine, cytarabine, G-CSF), FLAG-IDA (fludarabine, cytarabine, idarubicin, G-CSF), FLAG-MITO (mitoxantrone, fludarabine, cytarabine, G-CSF), FLAMSA (fludarabine, cytarabine, amsacrine), FLAMSA-BU (fludarabine, cytarabine, amsacrine, busulfan), FLAMSA-MEL (fludarabine, cytarabine, amsacrine, melphalan), GVD (gemcitabine, vinorelbine, pegylated liposomal doxorubicin), GEMOX (gemcitabine, oxaliplatin), IAC (idarubicin×3 days plus cytarabine×7 days), ICE (ifosfamide, carboplatin, etoposide), IVAC (etoposide, cytarabine, ifosfamide), m-BACOD (methotrexate, bleomycin, doxorubicin, cyclophosphamide, vincristine, dexamethasone), MACOP-B (methotrexate, leucovorin, doxorubicin, cyclophosphamide, vincristine, prednisone, bleomycin), MINE (mesna, ifosfamide, novantrone, etoposide), MOPP (mechlorethamine, vincristine, procarbazine, prednisone), MVP (mitomycin, vindesine, cisplatin), PACE (platinum agent, doxorubicin, cyclophosphamide, etoposide), PEB (cisplatin, etoposide, bleomycin), POMP (6-mercaptopurine, vincristine, methotrexate, prednisone), ProMACE-MOPP (methotrexate, doxorubicin, cyclophosphamide, etoposide, mechlorethamine, vincristine, procarbazine, prednisone), ProMACE-CytaBOM (prednisone, doxorubicin, cyclophosphamide, etoposide, cytarabine, bleomycin, vincristine, methotrexate, leucovorin), RVD (lenalidomide, bortezomib, dexamethasone), Stanford V (doxorubicin, mechlorethamine, bleomycin, vinblastine, vincristine, etoposide, prednisone), Thal/Dex (thalidomide, dexamethasone), VAD (vincristine, doxorubicin, dexamethasone), VAMP (vincristine, amethopterin, 6-mercaptopurine and prednisone, or vincristine, doxorubicin, methotrexate and prednisone, or vincristine, doxorubicin and methylprednisolone), VAPEC-B (vincristine, doxorubicin, prednisone, etoposide, cyclophosphamide, bleomycin), VD-PACE (bortezomib, dexamethasone, platinum agent, doxorubicin, cyclophosphamide, etoposide), and VTD-PACE (bortezomib, thalidomide, dexamethasone, platinum agent, doxorubicin, cyclophosphamide, etoposide).

In a specific embodiment, the combination chemotherapy that the human patient has failed is therapy with cyclophosphamide and prednisone. In a specific embodiment, the combination chemotherapy that the human patient has failed is a low-dose cyclophosphamide and prednisone regimen. A low-dose cyclophosphamide and prednisone regimen is a regimen where less than about 900 mg/m$^2$ per dose per day of intravenous cyclophosphamide is administered for less than 8 doses, and less than 2 mg/kg per dose, given twice per day, of oral prednisone is administered. In a specific embodiment, the combination chemotherapy is the low-dose cyclophosphamide and prednisone regimen described in Gross et al., 2012, Am J Transplant 12:3069-3075, as follows: a total of six cycles of therapy is given, and the cycles are given every 3 weeks; 600 mg/m$^2$ intravenous cyclophosphamide is given on day 1 of each cycle, and 1 mg/kg oral prednisone is given twice per day on days 1-5 of each cycle.

In a specific embodiment, the combination chemotherapy that the human patient has failed is therapy with cyclophosphamide and methylprednisolone. In a specific embodiment, the combination chemotherapy that the human patient has failed is a low-dose cyclophosphamide and methylprednisolone regimen. In a specific embodiment, the combination chemotherapy is the low-dose cyclophosphamide and methylprednisolone regimen is as described in Gross et al., 2012, Am J Transplant 12:3069-3075, as follows: a total of six cycles of therapy is given, and the cycles are given every 3 weeks; 600 mg/m$^2$ intravenous cyclophosphamide is given on day 1 of each cycle, and 0.8 mg/kg intravenous methylprednisolone is given every 12-hr on days 1-5 of each cycle.

In a specific embodiment, the combination chemotherapy that the human patient has failed is therapy with cyclophosphamide, prednisone, and methylprednisolone. In a specific embodiment, the combination chemotherapy that the human patient has failed is therapy with gemcitabine and vinorelbine. In a specific embodiment, the combination chemotherapy that the human patient has failed is therapy with methotrexate and temozolomide. In a specific embodiment, the combination chemotherapy that the human patient has failed is therapy with methotrexate, temozolomide and cytarabine. In a specific embodiment, the combination chemotherapy that the human patient has failed is therapy with prednisone and cyclophosphamide. In a specific embodiment, the combination chemotherapy that the human patient has failed is therapy with vincristine and cyclophosphamide. In a specific embodiment, the combination chemotherapy that the human patient has failed is therapy with doxorubicin, vincristine, prednisone, and methotrexate. In a specific embodiment, the combination chemotherapy that the human patient has failed is therapy with vinblastine, lomustine, and cytarabine. In a specific embodiment, the combination chemotherapy that the human patient has failed is COP. In a specific embodiment, the combination chemotherapy that the human patient has failed is BEACOPP. In a specific embodiment, the combination chemotherapy that the human patient has failed is CHOP. In a specific embodiment, the combination chemotherapy that the human patient has failed is therapy with cyclophosphamide, doxorubicin, vincristine, prednisone, cytarabine, methotrexate, and dexamethasone. In a specific embodiment, the combination chemotherapy that the human patient has failed is IVAC. In a specific embodiment, the combination chemotherapy that the human patient has failed is ESHAP. In a specific embodiment, the combination chemotherapy that the human patient has failed is therapy with melphalan and dexamethasone. In a specific embodiment, the combination chemotherapy that the human patient has failed is ProMACE-CytaBOM. In a specific embodiment, the combination chemotherapy that the human patient has failed is CHOP. In a specific embodiment, the combination chemotherapy that the human patient has failed is DA-EPOCH.

In a specific embodiment, the combination chemotherapy that the human patient has failed comprises any of the combinations of chemotherapeutic agents or chemotherapeutic regimens described above. In a specific embodiment, the combination chemotherapy that the human patient has failed consists essentially of any of the combinations of chemotherapeutic agents or chemotherapeutic regimens described above.

In a specific embodiment, when the human patient has failed multiple different combination chemotherapies to treat the EBV-LPD, at least one of the multiple different combination chemotherapies is any of the combinations of chemotherapeutic agents or chemotherapeutic regimens described above. In a specific embodiment, when the human patient has failed multiple different combination chemotherapies to treat the EBV-LPD, at least one of the multiple different combination chemotherapies comprises any of the combinations of chemotherapeutic agents or chemotherapeutic regimens described above. In a specific embodiment, when the human patient has failed multiple different combination chemotherapies to treat the EBV-LPD, at least one of the multiple different combination chemotherapies consists essentially of any of the combinations of chemotherapeutic agents or chemotherapeutic regimens described above.

Radiation therapies use high-energy radiation to kill cancer cells by damaging their DNA. The radiation therapy that the human patient has failed, according to the invention, can be any known in the art for treatment of a LPD. Exemplary radiation therapies include, but are not limited to: conventional external beam radiation therapy, stereotactic radiation therapy, intensity-modulated radiation therapy, volumetric modulated arc therapy, particle therapy, auger therapy, brachytherapy, and radioisotope therapy.

In various embodiments, wherein the EBV-LPD is a disorder of cells of B cell lineage, in addition to failing therapy with any of the combination chemotherapies and/or radiation therapies described above, the human patient also has failed therapy with an anti-CD20 monoclonal antibody (alone or in combination with other therapies for the EBV-LPD). The anti-CD20 monoclonal antibody can be any known in the art. In specific embodiments, the anti-CD20 monoclonal antibody is a chimeric antibody or a humanized antibody. In specific embodiments, the anti-CD20 monoclonal antibody is a monovalent antibody or multivalent (e.g., bivalent) antibody. In certain embodiments, the anti-CD20 monoclonal antibody is a monospecific antibody or multispecific (e.g., bispecific) antibody. In specific embodiments, the anti-CD20 monoclonal antibody is conjugated with a cytotoxic agent; alternatively, the anti-CD20 monoclonal antibody can be unconjugated. Exemplary anti-CD20 monoclonal antibodies include, but are not limited to: rituximab, obinutuzumab, ocrelizumab ofatumumab, ibritumomab tiuxetan, tositumomab, and veltuzumab. In a specific embodiment, the anti-CD20 monoclonal antibody is rituximab. In a specific embodiment, the human patient has failed R-CEOP (a therapy regimen with cyclophosphamide, etoposide, vincristine, prednisone, and rituximab). In a specific embodiment, the human patient has failed R-GEMOX (a therapy regimen with gemcitabine, oxaliplatin, and rituximab). In a specific embodiment, the human patient has failed R-COP (a therapy regimen with cyclophosphamide, vincristine, prednisone/prednisolone, and rituximab). In a specific embodiment, the human patient has failed R-CHOP (a therapy regimen with cyclophosphamide, doxorubicin, vincristine, prednisone, and rituximab). In a specific embodiment, the human patient has failed a therapy with rituximab, cyclophosphamide and prednisone. In a specific embodiment, the human patient has failed a therapy with rituximab, cyclophosphamide and methylprednisolone. In a specific embodiment, the human patient has failed a treatment regimen described in Gross et al., 2012, Am J Transplant 12:3069-3075, as follows: a total of six cycles of therapy is given, and the cycles are given every 3 weeks; 600 mg/m$^2$ intravenous cyclophosphamide is given on day 1 of each cycle for six cycles, 1 mg/kg oral prednisone is given twice a day (or 0.8 mg/kg intravenous methylprednisolone is given every 12-hr) on days 1-5 of each cycle for six cycles, and 375 mg/m² intravenous rituximab is given on days 1, 8, and 15 of each cycle for the first two cycles.

As will be evident from the foregoing, where a human patient has failed both a combination chemotherapy to treat the EBV-LPD and a therapy with an anti-CD20 monoclonal antibody to treat the EBV-LPD, the combination chemotherapy and the therapy with the anti-CD20 monoclonal antibody can be combined in a single therapy regimen, or can be in separate therapy regimens administered over different time periods to the human patient.

4.2. A Population of Allogeneic T Cells Restricted by an Shared HLA Allele with the EBV-LPD According to the invention, a population of allogeneic T cells comprising EBV-specific T cells is administered to the human patient. The population of allogeneic T cells that is administered to the human patient is restricted by an HLA allele shared with cells of the EBV-LPD. In some embodiments, this HLA allele restriction is ensured by ascertaining the HLA assignment of cells of the EBV-LPD, and selecting a population of allogeneic T cells comprising EBV-specific T cells (or a T cell line from which to derive the population of allogeneic T cells) restricted by an HLA allele of such cells. In other embodiments, when ascertaining the HLA assignment of cells of the EBV-LPD is not possible and a human patient has not been the recipient of a transplant, this HLA allele restriction is ensured by ascertaining the HLA assignment of the human patient (e.g., by using non-LPD cells or tissue from the human patient), and selecting a population of allogeneic T cells comprising EBV-specific T cells (or a T cell line from which to derive the population of allogeneic T cells) restricted by an HLA allele of the human patient. In other embodiments, when ascertaining the HLA assignment of cells of the EBV-LPD is not possible and the human patient has been the recipient of a transplant, this HLA allele restriction is ensured by determining the origin of the EBV-LPD (whether transplant donor or recipient (the human patient)), ascertaining the HLA assignment of the origin of the EBV-LPD (transplant donor or the human patient, as the case may be), and selecting a population of allogeneic T cells comprising EBV-specific T cells (or a T cell line from which to derive the population of allogeneic T cells) restricted by an HLA allele of the origin of the EBV-LPD. When determining the origin of the EBV-LPD is not possible in such embodiments, this HLA allele restriction is ensured by ascertaining the HLA assignment of both the human patient and the transplant donor, and selecting a population of allogeneic T cells comprising EBV-specific T cells (or a T cell line from which to derive the population of allogeneic T cells) restricted by an HLA allele shared by both the human patient and the transplant donor.

The origin of the EBV-LPD can be determined by any method known in the art, for example by analyzing variable tandem repeats (VTRs), a method that uses unique DNA signature of small DNA sequences of different people to distinguish between the recipient and the donor of a transplant; or by looking for the presence or absence of chromosome Y if the donor and the recipient of a transplant are of different sexes, done by cytogenetics or by FISH (fluorescence in situ hybridization).

In some embodiments of ascertaining an HLA assignment, at least 4 HLA loci (preferably HLA-A, HLA-B, HLA-C, and HLA-DR) are typed. In some embodiments of ascertaining an HLA assignment, 4 HLA loci (preferably HLA-A, HLA-B, HLA-C, and HLA-DR) are typed. In some embodiments of ascertaining an HLA assignment, 6 HLA loci are typed. In some embodiments of ascertaining an HLA assignment, 8 HLA loci are typed.

In specific embodiments, in addition to being restricted by an HLA allele shared with the EBV-LPD, the population of allogeneic T cells comprising EBV-specific T cells shares at least 2 out of 8 HLA alleles (for example, two HLA-A alleles, two HLA-B alleles, two HLA-C alleles, and two HLA-DR alleles) with cells of the EBV-LPD. In some embodiments, this sharing is ensured by ascertaining the HLA assignment of cells of the EBV-LPD, and selecting a population of allogeneic T cells comprising EBV-specific T cells (or a T cell line from which to derive the population of allogeneic T cells) that shares at least 2 out of 8 HLA alleles with such cells. In other embodiments, when ascertaining the HLA assignment of cells of the EBV-LPD is not possible and the human patient has not been the recipient of a transplant, this sharing is ensured by ascertaining the HLA assignment of the human patient (e.g., by using non-LPD cells or tissue from the human patient), and selecting a population of allogeneic T cells comprising EBV-specific T cells (or a T cell line from which to derive the population of allogeneic T cells) that shares at least 2 out of 8 HLA alleles with the human patient. In other embodiments, when ascertaining the HLA assignment of cells of the EBV-LPD is not possible and the human patient has been the recipient of a transplant, this sharing is ensured by determining the origin of the EBV-LPD (whether transplant donor or recipient (the human patient)), ascertaining the HLA assignment of the origin of the EBV-LPD (transplant donor or the human patient, as the case may be), and selecting a population of allogeneic T cells comprising EBV-specific T cells (or a T cell line from which to derive the population of allogeneic T cells) that shares at least 2 out of 8 HLA alleles with the origin of the EBV-LPD. When determining the origin of the EBV-LPD is not possible in such embodiments, this is ensured by ascertaining the HLA assignment of both the human patient and the transplant donor, and selecting a population of allogeneic T cells comprising EBV-specific T cells (or a T cell line from which to derive the population of allogeneic T cells) that shares at least 2 out of 8 HLA alleles with both the human patient and the transplant donor.

The HLA assignment (i.e., the HLA loci type) can be ascertained (i.e., typed) by any method known in the art. Non-limiting exemplary methods for ascertaining the HLA assignment can be found in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Hurley, "DNA-based typing of HLA for transplantation." in Leffell et al., eds., 1997, Handbook of Human Immunology, Boca Raton: CRC Press; Dunn, 2011, Int J Immunogenet 38:463-473; Erlich, 2012, Tissue Antigens, 80:1-11; Bontadini, 2012, Methods, 56:471-476; and Lange et al., 2014, BMC Genomics 15: 63.

In general, high-resolution typing is preferable for HLA typing. The high-resolution typing can be performed by any method known in the art, for example, as described in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Flomenberg et al., Blood, 104:1923-1930; Kogler et al., 2005, Bone Marrow Transplant, 36:1033-1041; Lee et al., 2007, Blood 110:4576-4583; Erlich, 2012, Tissue Antigens, 80:1-11; Lank et al., 2012, BMC Genomics 13:378; or Gabriel et al., 2014, Tissue Antigens, 83:65-75. In specific embodiments, the methods of treating an EBV-LPD as described herein further comprise prior to the administering step a step of ascertaining at least one HLA allele of cells of the EBV-LPD by high-resolution typing.

The HLA allele by which the population of allogeneic T cells is restricted can be determined by any method known in the art, for example, as described in Trivedi et al., 2005, Blood 105:2793-2801; Barker et al., 2010, Blood 116:5045-5049; Hasan et al., 2009, J Immunol, 183:2837-2850; or Doubrovina et al., 2012, Blood 120:1633-1646.

Preferably, the HLA allele by which the population of allogeneic T cells is restricted and is shared with cells of the EBV-LPD is defined by high-resolution typing. Preferably, the HLA alleles that are shared between the population of allogeneic T cells and cells of the EBV-LPD are defined by high-resolution typing. Most preferably, both the HLA allele by which the population of allogeneic T cells is restricted and is shared with cells of the EBV-LPD, and the HLA alleles that are shared between the population of allogeneic T cells and cells of the EBV-LPD are defined by high-resolution typing.

4.3. Obtaining or Generating a Population of Allogeneic T Cells Comprising EBV-specific T Cells The population of allogeneic T cells comprising EBV-specific T cells that is administered to the human patient can be generated by a method known in the art, or can be selected from a preexisting bank (collection) of cryopreserved T cell lines (each T cell line comprising EBV-specific T cells) generated by a method known in the art, and thawed and preferably expanded prior to administration. Preferably, unique identifier for each T cell line in the bank is associated with information as to which HLA allele(s) the respective T cell line is restricted, and optionally also information as to the HLA assignment of the respective T cell line. The population of allogeneic T cells and the T cell lines in the bank are preferably obtained or generated by methods described below.

In various embodiments, the methods of treating an EBV-LPD further comprise prior to the administering step a step of obtaining the population of allogeneic T cells.

In specific embodiments, the step of obtaining the population of allogeneic T cells comprises fluorescence activated cell sorting for EBV-positive T cells from a population of blood cells. In a specific embodiment, the population of blood cells are peripheral blood mononuclear cells (PBMCs) isolated from a blood sample(s) obtained from a human donor. The fluorescence activated cell sorting can be performed by any method known in the art, which normally involves staining the population of blood cells with an antibody that recognizes at least one EBV antigen before the sorting step.

In specific embodiments, the step of obtaining the population of allogeneic T cells comprises generating the population of allogeneic T cells in vitro. The population of allogeneic T cells can be generated in vitro by any method known in the art. Non-limiting exemplary methods of generating the population of allogeneic T cells can be found in Koehne et al., 2000, Blood 96:109-117; Koehne, et al., 2002, Blood 99:1730-1740; O'Reilly et al., 2007, Immunol Res 38:237-250; Barker et al., 2010, Blood 116:5045-5049; O'Reilly et al., 2011, Best Practice & Research Clinical Haematology 24:381-391; and Doubrovina et al., 2012, Blood 119:2644-2656.

In certain embodiments, the step of generating the population of allogeneic T cells in vitro comprises sensitizing (i.e., stimulating) allogeneic T cells to one or more EBV antigens so as to produce EBV-specific T cells. The allogeneic T cells that are used for generating the population of allogeneic T cells in vitro can be isolated from the donor of the allogeneic T cells by any method known in the art, for example, as described in Koehne, et al., 2002, Blood 99:1730-1740; O'Reilly et al., 2007, Immunol Res. 38:237-250; or Barker et al., 2010, Blood 116:5045-5049. In a specific embodiment, the allogeneic T cells are enriched from peripheral blood lymphocytes separated from PBMCs of the donor of the allogeneic T cells. In a further specific embodiment, T cells are enriched from peripheral blood lymphocytes separated from PBMCs of the donor of the allogeneic T cells by depletion of adherent monocytes followed by depletion of natural killer cells. In various embodiments, the allogeneic T cells are cryopreserved for storage. In a specific embodiment, wherein the allogeneic T cells are cryopreserved, the cryopreserved allogeneic T cells are thawed and expanded in vitro before sensitizing. In a specific embodiment, wherein the allogeneic T cells are cryopreserved, the cryopreserved allogeneic T cells are thawed and then sensitized, but not expanded in vitro before sensitizing, and then optionally expanded. In specific embodiments, the allogeneic T cells are cryopreserved after sensitizing (sensitizing produces the EBV-specific T cells). In a specific embodiment, wherein the allogeneic T cells are cryopreserved after sensitizing, the cryopreserved allogeneic T cells are thawed and expanded in vitro to produce the population of allogeneic T cells comprising EBV-specific T cells. In another specific embodiment, wherein the allogeneic T cells are cryopreserved after sensitizing, the cryopreserved allogeneic T cells are thawed but not expanded in vitro to produce the population of allogeneic T cells comprising EBV-specific T cells. In other various embodiments, the allogeneic T cells are not cryopreserved. In a specific embodiment, wherein the allogeneic T cells are not cryopreserved, the allogeneic T cells are expanded in vitro before sensitizing. In a specific embodiment, wherein the allogeneic T cells are not cryopreserved, the allogeneic T cells are not expanded in vitro before sensitizing. In specific embodiments, the step of generating the population of allogeneic T cells in vitro further comprises, after sensitizing, cryopreserving the allogeneic T cells.

In specific embodiments, the methods of treating an EBV-LPD as described herein further comprise, before the administering step, steps of thawing cryopreserved EBV-antigen sensitized allogeneic T cells, and expanding the allogeneic T cells in vitro, to produce the population of allogeneic T cells.

In certain embodiments, the step of generating the population of allogeneic T cells in vitro comprises sensitizing allogeneic T cells using EBV-transformed B cells (i.e., contacting allogeneic T cells with EBV-transformed B cells). B cells transformed by EBV strain B95.8, for example, can be used for this purpose.

In certain embodiments, the step of generating the population of allogeneic T cells in vitro comprises sensitizing allogeneic T cells using dendritic cells (preferably, the dendritic cells are derived from the donor of allogeneic T cells). In specific embodiments, the step of sensitizing allogeneic T cells using dendritic cells comprises loading the dendritic cells with at least one immunogenic peptide derived from one or more EBV antigens. In specific embodiments, the step of sensitizing allogeneic T cells using dendritic cells comprises loading the dendritic cells with a pool of overlapping peptides derived from one or more EBV antigens.

In certain embodiments, the step of generating the population of allogeneic T cells in vitro comprises sensitizing allogeneic T cells using cytokine-activated monocytes (preferably, the cytokine-activated monocytes are derived from the donor of allogeneic T cells). In specific embodiments, the step of sensitizing allogeneic T cells using cytokine-activated monocytes comprises loading the cytokine-activated monocytes with at least one immunogenic peptide derived from one or more EBV antigens. In specific embodiments, the step of sensitizing allogeneic T cells using cytokine-activated monocytes comprises loading the cytokine-activated monocytes with a pool of overlapping peptides derived from one or more EBV antigens.

In certain embodiments, the step of generating the population of allogeneic T cells in vitro comprises sensitizing allogeneic T cells using peripheral blood mononuclear cells (preferably, the peripheral blood mononuclear cells are derived from the donor of allogeneic T cells). In specific embodiments, the step of sensitizing allogeneic T cells using peripheral blood mononuclear cells comprises loading the peripheral blood mononuclear cells with at least one immunogenic peptide derived from one or more EBV antigens. In specific embodiments, the step of sensitizing allogeneic T cells using peripheral blood mononuclear cells comprises loading the peripheral blood mononuclear cells with a pool of overlapping peptides derived from one or more EBV antigens.

In certain embodiments, the step of generating the population of allogeneic T cells in vitro comprises sensitizing allogeneic T cells using artificial antigen-presenting cells (AAPCs). In specific embodiments, the step of sensitizing allogeneic T cells using AAPCs comprises loading the AAPCs with at least one immunogenic peptide derived from one or more EBV antigens. In specific embodiments, the step of sensitizing allogeneic T cells using AAPCs comprises loading the AAPCs with a pool of overlapping peptides derived from one or more EBV antigens. In specific embodiments, the step of sensitizing allogeneic T cells using AAPCs comprises engineering the AAPCs to express at least one immunogenic EBV peptide or protein in the AAPCs.

In various embodiments, the pool of peptides is a pool of overlapping peptides spanning an antigen of EBV. In various embodiments, the pool of peptides is a pool of overlapping peptides spanning more than one antigen of EBV. In a specific embodiment, the pool of overlapping peptides is a pool of overlapping pentadecapeptides.

In specific embodiments, the population of allogeneic T cells has been cryopreserved for storage before administering. In specific embodiments, the population of allogeneic T cells has not been cryopreserved for storage before administering. In certain embodiments, the methods of treating an EBV-LPD as described herein further comprise, before the administering step, a step of thawing a cryopreserved form of the population of allogeneic T cells.

In various embodiments, the population of allogeneic T cells is derived from a T cell line. In specific embodiments, the T cell line has been cryopreserved for storage before administering. In specific embodiments, the T cell line has not been cryopreserved for storage before administering. In some embodiments, the T cell line has been expanded in vitro to derive the population of allogeneic T cells. In other embodiments, the T cell line has not been expanded in vitro to derive the population of allogeneic T cells. The T cell line can be sensitized to one or more EBV antigens (so as to produce EBV-specific T cells, for example, by a sensitizing step described above) before or after cryopreservation (if the T cell line has been cryopreserved), and before or after expanding in vitro (if the T cell line has been expanded in vitro). In certain embodiments, the methods of treating an EBV-LPD as described herein further comprise, before the administering step, a step of selecting the T cell line from a bank of a plurality of cryopreserved T cell lines (preferably each comprising EBV-specific T cells). Preferably, unique identifier for each T cell line in the bank is associated with information as to which HLA allele(s) the respective T cell line is restricted, and optionally also information as to the HLA assignment of the respective T cell line. In certain embodiments, the methods of treating an EBV-LPD as described herein further comprise, before the administering step, a step of thawing a cryopreserved form of the T cell line. In specific embodiments, the methods of treating an EBV-LPD as described herein further comprises, before the administering step, a step of expanding the T cell line (for example, after thawing a cryopreserved form of the T cell line) in vitro. The T cell line and the plurality of cryopreserved T cell lines can be generated by any method known in the art, for example, as described in Koehne, et al., 2002, Blood 99:1730-1740; O'Reilly et al., 2007, Immunol Res. 38:237-250; Barker et al., 2010, Blood 116:5045-5049, or as describe above for generating the population of allogeneic T cells in vitro.

The population of allogeneic T cells comprising EBV-specific T cells that is administered to the human patient comprises CD8+ T cells, and in a specific embodiment also comprises CD4+ T cells.

The EBV-specific T cells administered in accordance with the methods described herein recognize at least one antigen of EBV. In specific embodiments, the EBV-specific T cells administered in accordance with the methods described herein recognizes an EBV antigen that is EBNA1, EBNA2, EBNA3A, EBNA3B, EBNA3C, LMP1 or LMP2.

4.4. Administration and Dosage

The route of administration of the population of allogeneic T cells and the amount to be administered to the human patient can be determined based on the condition of the human patient and the knowledge of the physician. Generally, the administration is intravenous.

In certain embodiments, the administering is by infusion of the population of allogeneic T cells. In some embodiments, the infusion is bolus intravenous infusion. In certain embodiments, the administering comprises administering at least about $1 \times 10^5$ T cells of the population of allogeneic T cells per kg per dose per week to the human patient. In some embodiments, the administering comprises administering about $1 \times 10^6$ to about $2 \times 10^6$ T cells of the population of allogeneic T cells per kg per dose per week to the human patient. In a specific embodiment, the administering comprises administering about $1 \times 10^6$ T cells of the population of allogeneic T cells per kg per dose per week to the human patient. In another specific embodiment, the administering comprises administering about $2 \times 10^6$ T cells of the population of allogeneic T cells per kg per dose per week to the human patient.

In certain embodiments, the methods of treating an EBV-LPD as described herein comprise administering at least 2 doses of the population of allogeneic T cells to the human patient. In specific embodiments, the methods of treating an EBV-LPD as described herein comprise administering 2, 3, 4, 5, or 6 doses of the population of allogeneic T cells to the human patient.

In certain embodiments, the methods of treating an EBV-LPD as described herein comprise administering a first cycle of one dose per week of the population of allogeneic T cells for 3 consecutive weeks followed by a washout period during which no dose of the population of allogeneic T cells is administered, followed by a second cycle of the one dose per week of the population of allogeneic T cells for 3 consecutive weeks. In certain embodiments, the methods of treating an EBV-LPD as described herein comprise administering at least two cycles of one dose per week of the population of allogeneic T cells for 3 consecutive weeks, each cycle separated by a washout period during which no dose of the population of allogeneic T cells is administered. In specific embodiments, the methods of treating an EBV-LPD as described herein comprise administering two, three, four, five, or six cycles of one dose per week of the population of allogeneic T cells for 3 consecutive weeks, each cycle separated by a washout period during which no dose of the population of allogeneic T cells is administered. In a specific embodiment, the washout period is about three weeks. Preferably, an additional cycle is administered only when the previous cycle has not exhibited toxicity (for example, no grade 3-5 serious adverse events, graded according to NCI CTCAE 4.0).

In certain embodiments, a first dosage regimen described herein is carried out for a first period of time, followed by a second and different dosage regimen described herein that is carried out for a second period of time, wherein the first period of time and the second period of time are optionally separated by a washout period (for example, about three weeks). Preferably, the second dosage regimen is carried out only when the first dosage regimen has not exhibited toxicity (for example, no grade 3-5 serious adverse events, graded according to NCI CTCAE 4.0).

The term "about" shall be construed so as to allow normal variation.

4.5. Serial Treatment with Different T Cell Populations

In certain embodiments, the methods of treating an EBV-LPD further comprise, after administering to the human patient the population of allogeneic T cells, administering to the human patient a second population of allogeneic T cells comprising EBV-specific T cells; wherein the second population of allogeneic T cells is restricted by a different HLA allele shared with cells of the EBV-LPD. The second population of allogeneic T cells can be administered by any route and any dosage/administration regimen as described in Section 4.4. In a specific embodiment, the methods of treating an EBV-LPD comprise administering a first cycle of one dose per week of the population of allogeneic T cells for 3 consecutive weeks followed by a washout period during which no dose of the population of allogeneic T cells is administered, followed by a second cycle of one dose per week of the second population of allogeneic T cells for 3 consecutive weeks. In a further specific embodiment, the washout period is about three weeks.

In certain embodiments, the human patient has no response, an incomplete response, or a suboptimal response (i.e., the human patient may still have a substantial benefit from continuing treatment, but has reduced chances of optimal long-term outcomes) after administering the population of allogeneic T cells and prior to administering the second population of allogeneic T cells.

In specific embodiments, two populations of allogeneic EBV-specific T cells that are each restricted by a different HLA allele shared with cells of the EBV-LPD are administered serially. In specific embodiments, three populations of allogeneic EBV-specific T cells that are each restricted by a different HLA allele shared with cells of the EBV-LPD are administered serially. In specific embodiments, four populations of allogeneic EBV-specific T cells that are each restricted by a different HLA allele shared with cells of the EBV-LPD are administered serially. In specific embodiments, more than four populations of allogeneic EBV-specific T cells that are each restricted by a different HLA allele shared with cells of the EBV-LPD are administered serially.

4.6. Patients

The human patient can be anyone who has an EBV-LPD and who has failed combination chemotherapy to treat the EBV-LPD (and in some embodiments, also has failed therapy with an anti-CD20 monoclonal antibody) and/or radiation therapy (and in some embodiments, also has failed therapy with an anti-CD20 monoclonal antibody).

LPDs are conditions in which lymphocytes are excessively proliferating, and can occur in immunocompromised patients. EBV-LPDs that can be treated by the methods described herein include, but are not limited to, B-cell hyperplasia, B-cell lymphoma (for example, diffuse large B-cell lymphoma), T-cell lymphoma, polymorphic or monomorphic EBV-LPD, EBV-positive Hodgkin's lymphoma, Burkitt lymphoma, autoimmune lymphoproliferative syndrome, and mixed PTLD (post-transplant lymphoproliferative disorder). In a specific embodiment, the EBV-LPD is an EBV-positive lymphoma (for example, and EBV-positive B-cell lymphoma). In specific embodiments, the EBV-LPD treated in accordance with a method described herein is present in the central nervous system of the human patient. In a specific embodiment, the EBV-LPD treated in accordance with a method described herein is present in the brain of the human patient.

In various embodiments, the human patient has been immunocompromised. In various embodiments, the human patient has been the recipient of a transplant. In some embodiments, the human patient has been the recipient of a solid organ transplant from a transplant donor. In some embodiments, the human patient has been the recipient of multiple organ transplants (for example, heart and lung transplants, or kidney and pancreas transplants). The solid organ transplant can be, but is not limited to, a kidney transplant, a liver transplant, a heart transplant, an intestinal transplant, a pancreas transplant, a lung transplant, or a combination thereof. In a specific embodiment, the solid organ transplant is a kidney transplant. In another specific embodiment, the solid organ transplant is a liver transplant. In some embodiments, the human patient has been the recipient of a hematopoietic stem cell transplant (HSCT) from a transplant donor. The HSCT can be a bone marrow transplant, a peripheral blood stem cell transplant, or a cord blood transplant. In specific embodiments, the population of allogeneic T cells is derived from a donor other than the transplant donor. In other specific embodiments, the population of allogeneic T cells is derived from the transplant donor. In various embodiments, the human patient has not been the recipient of a transplant.

In specific embodiments, the human patient is a patient infected with HIV.

In specific embodiments, the human patient has received immunosuppressant therapy (for example, after solid organ transplant). In a particular aspect of such specific embodiments, the dosage of the immunosuppressant given to the human patient has been reduced, and the human patient has failed the therapy for the EBV-LPD of reducing the immunosuppressant dosage.

In specific embodiments, the human patient has a primary immunodeficiency (for example, a genetic disorder that has caused immunodeficiency).

In other embodiments, the human patient has not been immunocompromised.

5. EXAMPLE

Certain embodiments provided herein are illustrated by the following non-limiting example, which demonstrates that the therapy with a population of allogeneic T cells comprising EBV-specific T cells according to the invention is effective in treating EBV-LPDs that are resistant to combination chemotherapy or radiation therapy, and are also resistant to therapy with rituximab, as a later line therapy with low toxicity.

5.1. Example

Eleven recipients of solid organ transplant (SOT) were referred to Memorial Sloan Kettering Cancer Center for treatment of EBV-LPD in the form of a lymphoma after prior systemic chemotherapy. All had previously received rituximab and at least two prior combination chemotherapy regimens. Nine were referred for either incomplete response (3) or progression of disease (6) while receiving combination chemotherapy regimens, while two were referred at the time of relapse after prior combination chemotherapy. Thus, all 11 patients had failed combination chemotherapy for the EBV-LPD.

Where possible the lymphoma was assessed for origin (SOT donor vs host). In instances where this was not possible, high resolution HLA testing of SOT donor tissue was performed for at least one allele with the goal of finding a line that was restricted by HLA alleles on both the host and the solid organ donor.

T cell lines were selected from a bank of allogeneic T cell lines (each comprising EBV-specific T cells) that shared at least 2/8 HLA alleles (A, B, C and DR) at high resolution with the patient and HLA restricted in recognition of EBV through an allele known to be expressed by the lymphoma or by alleles expressed by both the host and the solid organ donor tissue.

Patients received $2 \times 10^6$ T cells/kg/dose for 3 weekly doses. Patients could receive additional cycles of cells if they had no toxicity related to the T cell therapy (no Grade 3-5 serious adverse events, graded according to NCI CTCAE 4.0) 5 weeks after the start of therapy. Patients could receive subsequent cycles of cells from different allogeneic T cell lines, preferably restricted by different HLA alleles.

Some of the patients received additional cycles of T cells, and some received additional cycles of T cells from at least one different allogeneic T cell line restricted by a different HLA allele.

Seven of the eleven patients responded to therapy. One who responded received subsequent systemic chemotherapy for recurrence of low grade disease to which she did not fully respond and was again in partial remission after subsequent T cell therapy. Two out of the seven who responded received subsequent rituximab treatment and re-treatment with EBV-specific T cells. One patient with a complete response died of failure of the transplanted organ that had predated cellular therapy. Three patients presented with high disease burden that was rapidly progressive at initiation of therapy and progressed during the first cycle of T cell therapies and these patients did not receive subsequent cycles of T cell therapy.

In addition, one patient with CNS (central nervous system) involvement of EBV-LPD was treated with incomplete response to rituximab and radiation therapy alone. This patient continued rituximab and started radiation concomitant to his first cycle of treatment with EBV-specific T cells. EBV-LPDs present in the brain (i.e., with brain involvement) are especially difficult to treat by chemotherapies and radiation therapies, because many chemotherapeutic agents cannot cross the blood-brain barrier, and radiation therapies normally cause damages to the brain; however a partial remission was achieved with the patient with brain involvement. That first cycle of T cell therapy was graded NE (not evaluable) and he had a slight response at the end. After subsequent cycles he had near resolution while receiving EBV-specific T cells as the only therapy for the EBV-LPD.

The T cell treatments exhibited low toxicity.

The fact that the methods described herein can effectively treat EBV-LPDs in patients who have been solid organ transplant recipients is especially remarkable, considering that the population of allogeneic T cells administered usually can only persist for a short period of time (in general shorter than in hematopoietic stem cell transplant (HSCT) recipients), due to rejection of the administered allogeneic T cells by the patient's relatively intact immune system (relative to patients who are recipients of HSCT).

Some of the therapy regimens that the patients have received are listed below in Table 1.

TABLE 1

| Therapy Regimens |
|---|
| 1. 6 cycles ANHL0221 (cyclophosphamide, prednisone, methylnisolone + rituximab); 2. 6 cycles gemcitabine/vinorelbine |
| 1. 5 cycles R-CEOP 2. R-GEMOX 3. rituximab + bortezomib HD methotrexate & temozolomide w/ rituximab; cytarabine |
| 1. rituximab/prednisone/cyclophosphamide) 2. vincristine/rituximab/cyclophosphamide |
| 1. ANHL0131 (doxorubicin, vincristine, prednisone, IT methotrexate) 2. vinblastine, CCNU, and ARA-C 3. ANHL01P1 (COP-R) 4. BEACOPP |
| 1. Cyclophosphamide, prednisone, rituximab per ANHL0221 6 cycles R-CHOP; IT cytarabine; 5 day course IT methotrexate, ara-C, dexamethasone 3 cycles IVAC start |
| 1. tonsillectomy/adenoidectomy 2. ANHL 0221 (cyclophosphamide/prednisone/rituximab) + ganciclovir and cytogam 3. ANHL 01P1 group B w/ rituximab + ganciclovir and cytogam 4. valganciclovir outpatient 5. ganciclovir and cytogam 6. during cells - 4 cycles gemcitabine + vinorelbine |
| 1. melphalan-dexamethasone 2. promace-cytabom x 6 3. infusions of EBV-specific T-cells generated by Kenneth Lucas from HLA identical sister 4. - 2 courses CHOP |
| 1. 3 cycles of cyclophosphamide w/ rituximab; 2. two doses of high-dose methotrexate + rituximab with leucovorin rescue 3. temozolomide |

6. INCORPORATION BY REFERENCE

Various publications are cited herein, the disclosures of which are hereby incorporated by reference herein in their entireties.

What is claimed is:

1. A method of treating an EBV-LPD (Epstein-Barr Virus-associated lymphoproliferative disorder) in a human patient comprising administering to the human patient a population of allogeneic T cells comprising EBV-specific T cells; wherein the EBV-LPD is a disorder of cells of B cell lineage, wherein the human patient has failed a combination chemotherapy to treat the EBV-LPD and a therapy with an anti-CD20 monoclonal antibody to treat the EBV-LPD, and wherein the population of allogeneic T cells is restricted by an human leukocyte antigen (HLA) allele shared with cells of the EBV-LPD.

2. The method of claim 1, wherein the human patient also has failed a radiation therapy to treat the EBV-LPD.

3. The method of claim 1, wherein the EBV-LPD is an EBV-positive lymphoma.

4. The method of claim 1, wherein the EBV-LPD is present in the central nervous system of the human patient.

5. The method of claim 1, wherein the human patient has been the recipient of a solid organ transplant from a transplant donor.

6. The method of claim 1, wherein the human patient has been the recipient of a hematopoietic stem cell transplant from a transplant donor.

7. The method of claim 5, wherein the population of allogeneic T cells is derived from a donor other than the transplant donor.

8. The method of claim 1, further comprising, after administering to the human patient the population of allogeneic T cells, administering to the human patient a second population of allogeneic T cells comprising EBV-specific T cells; wherein the second population of allogeneic T cells is restricted by a different HLA allele shared with cells of the EBV-LPD.

9. The method of claim 1, wherein the EBV-LPD is diffuse large B-cell lymphoma.

10. The method of claim 1, wherein the human patient is infected with HIV.

11. The method of claim 2, wherein the EBV-LPD is an EBV-positive lymphoma.

12. The method of claim 2, wherein the EBV-LPD is present in the central nervous system of the human patient.

13. The method of claim 2, wherein the human patient has been the recipient of a solid organ transplant from a transplant donor.

14. The method of claim 2, wherein the human patient has been the recipient of a hematopoietic stem cell transplant from a transplant donor.

15. The method of claim 13, wherein the population of allogeneic T cells is derived from a donor other than the transplant donor.

16. The method of claim 2, further comprising, after administering to the human patient the population of allogeneic T cells, administering to the human patient a second population of allogeneic T cells comprising EBV-specific T cells; wherein the second population of allogeneic T cells is restricted by a different HLA allele shared with cells of the EBV-LPD.

17. The method of claim 2, wherein the EBV-LPD is diffuse large B-cell lymphoma.

18. The method of claim 2, wherein the human patient is infected with HIV.

19. The method of claim 6, wherein the population of allogeneic T cells is derived from a donor other than the transplant donor.

20. The method of claim 14, wherein the population of allogeneic T cells is derived from a donor other than the transplant donor.

21. The method of claim 1, wherein the EBV-LPD is resistant to the combination chemotherapy to treat the EBV-LPD and is resistant to the therapy with the anti-CD20 monoclonal antibody to treat the EBV-LPD.

22. The method of claim 2, wherein the EBV-LPD is resistant to the radiation therapy to treat the EBV-LPD.

23. The method of claim 1, wherein the anti-CD20 monoclonal antibody is rituximab.

24. The method of claim 2, wherein the anti-CD20 monoclonal antibody is rituximab.

25. A method of treating an EBV-LPD in a human patient comprising administering to the human patient a population of allogeneic T cells comprising EBV-specific T cells; wherein the EBV-LPD is diffuse large B-cell lymphoma, wherein the human patient has failed a combination chemotherapy to treat the EBV-LPD, and wherein the population of allogeneic T cells is restricted by an HLA allele shared with cells of the EBV-LPD.

26. The method of claim 25, wherein the EBV-LPD is resistant to the combination chemotherapy to treat the EBV-LPD.

27. The method of claim 25, wherein the human patient also has failed a radiation therapy to treat the EBV-LPD.

28. The method of claim 27, wherein the EBV-LPD is resistant to the radiation therapy to treat the EBV-LPD.

29. The method of claim 25, wherein the EBV-LPD is present in the central nervous system of the human patient.

30. The method of claim 25, wherein the human patient has been the recipient of a solid organ transplant from a transplant donor.

31. The method of claim 25, wherein the human patient has been the recipient of a hematopoietic stem cell transplant from a transplant donor.

32. The method of claim 30, wherein the population of allogeneic T cells is derived from a donor other than the transplant donor.

33. The method of claim 31, wherein the population of allogeneic T cells is derived from a donor other than the transplant donor.

34. The method of claim 25, wherein the human patient is infected with HIV.

35. The method of claim 25, further comprising, after administering to the human patient the population of allogeneic T cells, administering to the human patient a second population of allogeneic T cells comprising EBV-specific T cells; wherein the second population of allogeneic T cells is restricted by a different HLA allele shared with cells of the EBV-LPD.

36. The method of claim 1, wherein the population of allogeneic T cells is generated in vitro by sensitizing allogeneic T cells to one or more EBV antigens using EBV-transformed B cells.

37. The method of claim 25, wherein the population of allogeneic T cells is generated in vitro by sensitizing allogeneic T cells to one or more EBV antigens using EBV-transformed B cells.

* * * * *